(12) United States Patent
Perkins et al.

(10) Patent No.: US 7,458,963 B2
(45) Date of Patent: *Dec. 2, 2008

(54) METHODS, SYSTEMS, AND KITS FOR LUNG VOLUME REDUCTION

(75) Inventors: Rodney C. Perkins, Woodside, CA (US); Peter Soltesz, San Jose, CA (US); Robert Kotmel, Burlingame, CA (US)

(73) Assignee: PULMONx, Palo Alto, CA (US)

( * ) Notice: Subject to any disclaimer, the term of this patent is extended or adjusted under 35 U.S.C. 154(b) by 832 days.

This patent is subject to a terminal disclaimer.

(21) Appl. No.: 10/923,109

(22) Filed: Aug. 20, 2004

(65) Prior Publication Data

US 2005/0015106 A1   Jan. 20, 2005

Related U.S. Application Data

(63) Continuation of application No. 10/017,068, filed on Dec. 13, 2001, now Pat. No. 7,141,046, which is a continuation of application No. 09/606,320, filed on Jun. 28, 2000, now Pat. No. 6,878,141, which is a continuation-in-part of application No. 09/347,032, filed on Jul. 2, 1999, now Pat. No. 6,287,290.

(51) Int. Cl.
*A61M 31/00* (2006.01)
(52) U.S. Cl. .................................................. 604/514
(58) Field of Classification Search ............... 604/28, 604/35, 43, 516, 102.01, 102.02, 101.01, 604/101.04, 79, 96.01, 103.03, 104, 131; 128/207.15, 207.14, 200.26, 911
See application file for complete search history.

(56) References Cited

U.S. PATENT DOCUMENTS

| | | | |
|---|---|---|---|
| 3,322,126 A | 5/1967 | Rüsch et al. | |
| 3,498,286 A | 3/1970 | Polanyi et al. | |
| 3,669,098 A | 6/1972 | Takahashi | |
| 3,677,262 A | 7/1972 | Zukowski | |
| 3,776,222 A | 12/1973 | Smiddy | |

(Continued)

FOREIGN PATENT DOCUMENTS

WO      WO 92/10971      9/1992

(Continued)

OTHER PUBLICATIONS

Becker et al., "Lung volumes before and after lung volume reduction surgery," Am. J. Respir. Crit. Care Med., (1998) 157:1593-1599.

(Continued)

*Primary Examiner*—Manuel A Mendez
(74) *Attorney, Agent, or Firm*—Townsend and Townsend and Crew LLP

(57) ABSTRACT

Lung volume reduction is performed in a minimally invasive manner by isolating a lung tissue segment, optionally reducing gas flow obstructions within the segment, and aspirating the segment to cause the segment to at least partially collapse. Further optionally, external pressure may be applied on the segment to assist in complete collapse. Reduction of gas flow obstructions may be achieved in a variety of ways, including over inflation of the lung, introduction of mucolytic or dilation agents, application of vibrational energy, induction of absorption atelectasis, or the like. Optionally, diagnostic procedures on the isolated lung segment may be performed, typically using the same isolation/access catheter.

5 Claims, 16 Drawing Sheets

U.S. PATENT DOCUMENTS

| | | |
|---|---|---|
| 3,866,599 A | 2/1975 | Johnson |
| 3,913,568 A | 10/1975 | Carpenter |
| 4,041,936 A | 8/1977 | Carden |
| 4,086,919 A | 5/1978 | Bullard |
| 4,327,720 A | 5/1982 | Bronson et al. |
| 4,327,721 A | 5/1982 | Goldin et al. |
| 4,453,545 A | 6/1984 | Inoue |
| 4,468,216 A | 8/1984 | Muto |
| 4,567,882 A | 2/1986 | Heller |
| 4,716,896 A | 1/1988 | Ackerman |
| 4,742,819 A | 5/1988 | George |
| 4,784,133 A | 11/1988 | Mackin |
| 4,819,664 A | 4/1989 | Nazari |
| 4,846,153 A | 7/1989 | Berci |
| 4,850,371 A | 7/1989 | Broadhurst et al. |
| 4,862,874 A | 9/1989 | Kellner |
| 4,896,941 A | 1/1990 | Hayashi et al. |
| 4,949,716 A | 8/1990 | Chenoweth |
| 4,955,375 A | 9/1990 | Martinez |
| 4,958,932 A | 9/1990 | Kegelman et al. |
| 4,961,738 A | 10/1990 | Mackin |
| 4,976,710 A | 12/1990 | Mackin |
| 5,056,529 A | 10/1991 | de Groot |
| 5,143,062 A | 9/1992 | Peckham |
| 5,146,916 A | 9/1992 | Catalani |
| 5,165,420 A | 11/1992 | Strickland |
| 5,285,778 A | 2/1994 | Mackin |
| 5,309,903 A | 5/1994 | Long |
| 5,331,947 A | 7/1994 | Shturman |
| 5,361,753 A | 11/1994 | Pothmann et al. |
| 5,400,771 A | 3/1995 | Pirak et al. |
| 5,477,851 A | 12/1995 | Callaghan et al. |
| 5,499,625 A | 3/1996 | Frass et al. |
| 5,598,840 A | 2/1997 | Iund et al. |
| 5,642,730 A | 7/1997 | Baran |
| 5,645,519 A | 7/1997 | Lee et al. |
| 5,653,231 A | 8/1997 | Bell |
| 5,660,175 A | 8/1997 | Dayal |
| 5,682,880 A | 11/1997 | Brain |
| 5,707,352 A | 1/1998 | Sekins et al. |
| 5,752,921 A | 5/1998 | Orr |
| 5,893,841 A | 4/1999 | Glickman |
| 5,897,528 A | 4/1999 | Schultz |
| 5,928,264 A | 7/1999 | Sugarbaker et al. |
| 5,957,919 A | 9/1999 | Laufer |
| 6,174,323 B1 | 1/2001 | Biggs et al. |
| 6,258,100 B1 | 7/2001 | Alferness et al. |
| 6,287,290 B1 * | 9/2001 | Perkins et al. .............. 604/516 |
| 6,493,589 B1 | 12/2002 | Medhkour et al. |

FOREIGN PATENT DOCUMENTS

| | | |
|---|---|---|
| WO | WO 95/33506 | 12/1995 |
| WO | WO 98/48706 | 5/1998 |
| WO | WO 98/49191 | 5/1998 |
| WO | WO 99/01076 | 1/1999 |
| WO | WO 99/17827 | 4/1999 |

OTHER PUBLICATIONS

Bollinger et al., abstract, "Evaluation of high-risk lung resection candidates: pulmonary Haemondynamics versus exercise testing. A testing of five patients," Respiration, (1994) 61(4), pp. 181-186.

Clark Ojo et al., "Lung volume reduction surgery alters management of pulmonary nodules in patients with severe COPD," Chest, (1997) 112(6):1494-1500.

Coryllos and Birnbaum, "Studies in pulmonary gas absorption in bronchial obstruction. I. Two new methods for direct and indirect observation," Amer. J. Med. Sci., (1932) 183:317-326.

Coryllos and Birnbaum, "Studies in pulmonary gas absorption in bronchial obstruction. II. The behavior and absorption times of oxygen, carbon dioxid, nitrogen, hydrogen, helium, ethylene, nitrous oxid, ethyl chlorid, and ether in the lung," Amer. J. Med. Sci., (1932) 183:326-347.

Coryllos and Birnbaum, "Studies in pulmonary gas absorption in bronchial obstruction. III. A theory of air absorption in atelectasis," Amer. J. Med. Sci., (1932) 183:347-359.

Criner et al., "Effect of lung volume reduction surgery on diaphram strength," Am. J. Res. Crit. Care Med., (1998) 157:1578-1585.

Harada et al., "Re-expansion of refractory atelectasis using a bronchofiberscope with a balloon cuff,", Chest, (1983) 84(6):725-728.

Kotloff et al., "Comparison of short-term functional outcomes following unilateral and bilateral lung vloume reduction surgery," Chest, (1998) 113(4):890-895.

McKenna et al., abstract, "Patient selecetion criteria for lung volume reduciton surger," Journal of Thoracit and Cardiovascular Surgery, (1997) 114(6), pp. 957-964.

Melendez e tal., Abstract, "Predictive respiratory complication quotient predicts pulmonary complication in throacic surgical patients," (1998) 66(6), pp. 2164.

Sclafani, "Clearing the airways" AARC Times (1999) pp. 69-71, 97.

* cited by examiner

METHODS, SYSTEMS, AND KITS FOR LUNG VOLUME REDUCTION

CROSS-REFERENCES TO RELATED APPLICATIONS

This application is a continuation of U.S. application Ser. No. 10/017,068, filed on Dec. 13, 2001 now U.S. Pat. No. 7,141,046, which was a continuation of U.S. application Ser. No. 09/606,320, filed on Jun. 28, 2000 now U.S. Pat. No. 6,878,141, which was a continuation-in-part of U.S. application Ser. No. 09/347,032, filed on Jul. 2, 1999, now U.S. Pat. No. 6,287,290, the full disclosures of which are incorporated herein by reference.

BACKGROUND OF THE INVENTION

1. Field of the Invention

The present invention relates generally to medical methods, systems, and kits. More particularly, the present invention relates to methods and apparatus for effecting lung volume reduction by aspirating isolated segments of lung tissue.

Chronic obstructive pulmonary disease is a significant medical problem affecting 16 million people or about 6% of the U.S. population. Specific diseases in this group include chronic obstructive bronchitis, asthmatic (without bronchitis), and emphysema. While a number of therapeutic interventions are used and have been proposed, none are completely effective, and chronic obstructive pulmonary disease remains the fourth most common cause of death in the United States. Thus, improved and alternative treatments and therapies would be of significant benefit.

Of particular interest to the present invention, lung function in patients suffering from chronic obstructive pulmonary disease can be improved by reducing the effective lung volume, typically by resecting diseased portions of the lung. Resection of diseased portions of the lungs both promotes expansion of the non-diseased regions of the lung and decreases the portion of inhaled air which goes into the lungs but is unable to transfer oxygen to the blood. Lung reduction is conventionally performed in open chest or thoracoscopic procedures where the lung is resected, typically using stapling devices having integral cutting blades.

While effective in many cases, conventional lung reduction surgery is significantly traumatic to the patient, even when thoracoscopic procedures are employed. Such procedures often result in the unintentional removal of healthy lung tissue, and frequently leave perforations or other discontinuities in the lung which result in air leakage from the remaining lung. Even technically successful procedures can cause respiratory failure, pneumonia, death, and many older or compromised patients are not even candidates for these procedures. For these reasons, it would be desirable to provide improved methods, systems, and kits for performing lung volume reduction which overcome at least some of the shortcomings noted above.

2. Description of the Background Art

WO 99/01076 describes devices and methods for reducing the size of lung tissue by applying heat energy to shrink collagen in the tissue. In one embodiment, air may be removed from a bleb in the lung to reduce its size. Air passages to the bleb may then be sealed, e.g., by heating, to fix the size of the bleb. WO 98/49191 describes a plug-like device for placement in a lung air passage to isolate a region of lung tissue, where air is not removed from the tissue prior to plugging. WO 98/48706 describes the use of surfactants in lung lavage for treating respiratory distress syndrome.

Patents and applications relating to lung access, diagnosis, and treatment include U.S. Pat. Nos. 5,752,921; 5,707,352; 5,682,880; 5,660,175; 5,653,231; 5,645,519; 5,642,730; 5,598,840; 5,499,625; 5,477,851; 5,361,753; 5,331,947; 5,309,903; 5,285,778; 5,146,916; 5,143,062; 5,056,529; 4,976,710; 4,955,375; 4,961,738; 4,958,932; 4,949,716; 4,896,941; 4,862,874; 4,850,371; 4,846,153; 4,819,664; 4,784,133; 4,742,819; 4,716,896; 4,567,882; 4,453,545; 4,468,216; 4,327,721; 4,327,720; 4,041,936; 3,913,568 3,866,599; 3,776,222; 3,677,262; 3,669,098; 3,498,286; 3,322,126; WO 95/33506, and WO 92/10971.

Lung volume reduction surgery is described in many publications, including Becker et al. (1998) Am. J. Respir. Crit. Care Med. 157:1593-1599; Criner et al. (1998) Am. J. Respir. Crit. Care Med. 157:1578-1585; Kotloff et al. (1998) Chest 113:890-895; and Ojo et al. (1997) Chest 112:1494-1500.

The use of mucolytic agents for clearing lung obstructions is described in Sclafani (1999) AARC Times, January, 69-97. Use of a balloon-cuffed bronchofiberscope to reinflate a lung segment suffering from refractory atelectasis is described in Harada et al. (1983) Chest 84:725-728.

BRIEF SUMMARY OF THE INVENTION

The present invention provides improved methods, systems, and kits for performing lung volume reduction in patients suffering from chronic obstructive pulmonary disease or other conditions where isolation of a lung segment or reduction of lung volume is desired. The methods are minimally invasive with instruments being introduced through the mouth (endotracheally) and/or in some cases through the chest, (e.g., thoracoscopically), and rely on isolating the target lung tissue segment from other regions of the lung. Isolation is usually achieved by introducing an isolation/access catheter endotracheally to the air passages of a lung. By positioning a distal end of an isolation/access catheter within an air passage which opens into a target lung tissue segment, the segment may be isolated by occluding the air passage, typically by inflating an occlusion balloon or other structure on the catheter within the air passage. The target lung tissue segment may then be collapsed by aspirating air (and any other gases or liquids that may have been introduced) from the segment, typically through a lumen in the isolation/access catheter. Optionally, the air passage may then be sealed, for example by deploying a plug within the air passage. Suitable plugs include swellable collagen matrices which hydrate and expand within the air passage so that they fully occlude the passage. Other sealing methods include the use of tissue adhesives, such as fibrin glues, cyanoacrylate, etc.; the use of occlusive balloons; the use of self-expanding meshes, coils, and other occlusive structures; the use of energy-induced tissue fusion, such as radiofrequency tissue closure; and the like.

In a first particular aspect of the methods of the present invention, air flow through and from the target lung tissue segment will be enhanced prior to aspiration of the segment. It is an objective of the present invention to aspirate and reduce the volume of the lung tissue segment as completely as possible. In one instance, obstructions to gas flow within the target tissue segment are reduced prior to or during aspiration of the segment. Mucus and other obstructions within the target lung tissue segment (which is diseased and frequently subject to blockages) will interfere with substantially complete aspiration of the segment unless removed, disrupted, or otherwise addressed. In a second instance, where a lack of lung surfactant is a cause of the impeded air flow, the present invention will provide for administering a suitable surfactant prior to or during aspiration of the target lung tissue segment.

In a first specific instance, the present invention reduces gas flow obstructions by inflating the lung tissue segment to a pressure higher than normal respiratory inflation pressures. Optionally, portions or segments of the lung adjacent to the target lung segments may be partially deflated or under-ventilated at the same time that the target segment is being inflated at a higher than normal pressure. For example, airflow into adjacent lung segments-can be partially blocked to lower pressure in those segments, causing those segments to partially collapse. In a specific instance, a balloon can be used to partially block the bronchus of the lung with the target lung tissue segment.

Usually, the isolated lung tissue segment will be inflated to a pressure in the range from 60 cm $H_2O$ to 200 cm $H_2O$, preferably in the range from 100 cm-$H_2O$ to 150 cm $H_2O$, usually during the administration of general anesthesia (positive pressure ventilation). If a local anesthesia is being used, the pressure will usually be in the range from 10 cm $H_2O$ to 100 cm $H_2O$, preferably from 30 cm $H_2O$ to 60 cm $H_2O$. The duration of such "over inflation" will typically be in the range from one second to 600 seconds, preferably being in the range from 5 seconds to 60 seconds. Such lung inflation may be repeated more than one time. For example, the lung inflation may be carried out by inflating the isolated lung tissue segment in a pulsatile fashion. Over inflation will usually be performed using the isolation/access catheter which was used to isolate the lung tissue segment. Optionally, it would be possible to inflate regions of the lung percutaneously using a needle introduced through the chest, typically under thoracoscopic observation.

In a second specific instance, gas flow obstructions within the target lung tissue segment may be reduced by introducing an agent which clears the obstructions and/or dilates the air passages to permit gas flow around any blockages. Exemplary agents include mucolytic agents, bronchodilators, surfactants, desiccants, solvents, necrosing agents, absorbents, and the like. Such agents may be introduced through a catheter, typically through the isolation/access catheter which has been used to isolate the target lung tissue segment. Optionally, such agents may be heated, typically to a temperature in the range from 38° C. to 90° C. to enhance activity.

In a third specific instance, gas flow obstructions are reduced by delivering mechanical energy to the lung segment, typically vibratory energy which will break down at least some of the obstructions. Typically, the vibratory energy will be ultrasonic energy, more typically being ultrasonic energy having a frequency in the range from 20 kHz to 20 MHz, usually from 20 kHz to 5 MHz. The mechanical energy will usually be delivered to the target lung tissue segment through a non-compressible fluid introduced to the segment, usually through the isolation/access catheter. It will be appreciated that air is a poor transmission and absorption material for ultrasonic and other vibratory energy. Thus, introducing a non-compressible fluid, such as saline, contrast medium, treatment solution (e.g., mucolytic solution, surfactant solution, etc.), or the like, will enhance transmission and absorption of the energy throughout the target lung tissue segment. The vibratory energy may then be applied either through a catheter which has been introduced endotracheally and then into the target lung tissue segment, or externally using a hand-held or other ultrasonic probe intended to deliver ultrasonic energy transcutaneously. Typically, the vibrational treatment will last for time in the range from 5 seconds to 60 minutes, usually from 30 seconds to 30 minutes.

In a second aspect of the methods of the present invention, collapse of the target isolated lung tissue segment is enhanced by applying external pressure to the isolated segment. The external pressure will usually be applied through the chest, e.g., thoracoscopically. Most simply, a needle can be introduced to a pleural space over the lung, typically intracostally (between adjacent ribs). The pleural space can then be insufflated, e.g., carbon dioxide or other gas inflation medium introduced to the pleural space, in order to increase pressure on the lung and enhance collapse of the target segment. Simultaneously, the target segment will be aspirated so that the combined lowering of the internal pressure and raising of the external pressure work to substantially completely collapse the segment. Alternatively, the external pressure may be applied by inflating a balloon in the pleural space over the target lung tissue segment. Still further optionally, the external pressure may be applied by a probe which is engaged and pushed against at least a portion of the external surface of the lung overlying the target segment. Optionally, a thoracoscopically or other percutaneously placed needle could be used to puncture and aspirate a portion of the lung, typically in conjunction with a catheter-based aspiration as described elsewhere herein. For example, portions of the lung which could not be collapsed using an internal catheter could be targeted with an external needle by thoracoscopic visualization. Any puncture holes left in the lung could then be sealed with a suitable adhesive, such as a fibrin glue.

In a third aspect of the present invention, methods for reducing lung volume by isolating the lung tissue segment and aspirating the isolated segment are combined with diagnostic methods which permit, for example, determination of whether the segment which has been accessed and isolated is in fact diseased and should be collapsed. The diagnostic methods and steps may take a wide variety of forms. For example, the isolation/access catheter or other endotracheally introduced catheter may be used to measure air flow to and from the lung tissue segment to determine whether the air flow capabilities of that segment are impaired. Alternatively or additionally, the isolation/access catheter may be used to measure carbon dioxide concentrations within the target lung tissue segment. Other parameters which may be measured include forced expiratory volume, pressure, pressure/volume PN curves, segment compliance curves, work of breathing data, perfusion scans, bronchograms, or the like.

In a still further aspect of the methods of the present invention, a target lung tissue segment is isolated and aspirated, where the segment is collapsed to a volume which is no greater than 40% of its inflated size prior to aspiration, usually being no greater than 30%, and preferably being no greater than 20%. The inflated size is its maximum size at normal spontaneous respiratory pressures, assumed to be 40 cm $H_2O$ for patients undergoing positive pressure ventilation, the spontaneous respiratory pressure is assumed to be 90 cm $H_2O$. The change in volume may be determined by conventional techniques, such as thoracoscopy (X-ray), CT scans, MRI, ultrasound imaging, bronchograms, and the like.

Such efficient collapsing of the target lung tissue segment may be achieved in any of the ways discussed above. Additionally, it may be achieved by inducing absorption atelectasis prior to aspiration. Most simply, absorption atelectasis can be induced by insufflating the isolated lung tissue segment with high oxygen concentrations prior to aspiration. The oxygen concentrations in the insufflation gas should be at least 50% by volume, preferably 75% by volume, and more preferably being substantially pure oxygen.

The present invention further provides systems for performing intraluminal lung volume reduction procedures according to the methods of the present invention. The systems comprise at least an isolation or access catheter having a proximal end, a distal end, an occlusion element near the distal end, and at least one lumen therethrough. The isolation/access catheters are used for establishing access and isolation of a target lung tissue segment, typically by endotracheal introduction into the air passages of the lung. In a first system according to the present invention, the isolation/access catheter is combined with a sealing catheter which carries a closure element. A sealing catheter is adapted to be introduced through the lumen of the isolation/access catheter, and the closure element is adapted to be deployed from the isolation/access catheter within an air passage leading to the target tissue segment. The closure element typically comprises a swellable plug, such as a partially hydrated collagen plug. Deployment within the air passage thus permits the plug to swell in situ and completely block the air passage leading into the target tissue segment so that, once the segment is collapsed, air will not enter to reinflate the segment. Surprisingly, it has been found that such occlusion will substantially inhibit reinflation of the lung, and that there is little significant collateral air flow into the collapsed region.

In a second aspect, the systems of the present invention will combine the isolation/access catheter with a reagent capable of either clearing, dilating, or widening the air passages in order to facilitate substantially complete aspiration of the target tissue segments. Exemplary reagents have been set forth above.

In a third aspect, the systems of the present invention will combine the isolation/access catheter with probes intended for percutaneous introduction to apply external pressure over the lung. The probes may be in the form of a needle, a balloon, or a simple engagement element intended for pressing inwardly against the lung.

The present invention still further comprises kits which include at least an isolation/access catheter as described above. The kits will further comprise instructions for use according to any of the methods set forth above. For example, the instructions for use may set forth that the isolated lung tissue segment is to be over inflated in order to reduce blockages therein. Alternatively, the instructions for use may set forth that certain agents (as described above) are to be introduced to the segment in order to breakdown obstructive materials prior to aspiration. Still further, the kit instructions may set forth that the lung is to be externally collapsed by applying pressure or other external force to a target tissue segment prior to or simultaneous with aspiration of that segment. Still further, the instructions may set forth that the volume of the target lung tissue segment is to be reduced by at least the percentages set forth above. In all cases, the kits will usually further comprise packaging, such as a pouch, tray, tube, box, or the like for holding the kit components together with the instructions for use. The instructions for use may be printed on a separate sheet (commonly referred to as a package insert) and/or may be printed on the packaging itself. Usually, the kit components which will be introduced to the patient will be sterilized and packaged in a sterile manner within the kit.

DETAILED DESCRIPTION OF THE INVENTION

Lung volume reduction is performed by collapsing a target lung tissue segment, usually within sub-lobular regions of the lung which receive air through a single air passage, i.e., segment of the branching bronchus which deliver to and receive air from the alveolar regions of the lung. Such isolated lung tissue segments are first isolated and then collapsed by aspiration of the air (or other gases or liquids which may have been introduced, as discussed below) from the target lung tissue segment. Lung tissue has a very high percentage of void volume, so removal of internal gases can reduce the lung tissue to a small percentage of the volume which it has when fully inflated, i.e. inflated at normal inspiratory pressures. The exemplary and preferred percentages for the volume reduction are set forth above.

In particular, the present invention provides methods and apparatus for enhancing the aspiration and collapse of the target lung tissue segment. Such methods and apparatus may involve one or more of the following improvements. First, various approaches may be taken to remove or lessen obstructions to gas flow within the target tissue region. Second, methods and apparatus may be employed to apply external pressure over the lung to enhance the collapse achieved by internal aspiration. Third, aspiration of the gases within the target tissue segment may be enhanced by inducing absorption atelectasis prior to aspiration. Absorption atelectasis may be induced, for example, by introducing an oxygen-rich gas to the lung tissue segment, usually at least 50% oxygen by weight, more usually at least 75% oxygen by weight, and preferably substantially pure oxygen. Absorption atelectasis is a phenomena which occurs when an enriched oxygen mixture is inspired. The high oxygen concentration causes an increase in the partial oxygen pressure which in turn causes the rate of oxygen transfer into the capillary blood within the alveolar regions to increase greatly. The increased oxygen flux may increase so much that the net flow of gas into the blood exceeds the inspired flow of gas, causing the lung unit to become progressively smaller. Fourth, the access methods and apparatus may be used for performing in situ diagnosis, usually as part of the collapse procedure. Any one of a number of lung performance characteristics may be measured, typically by sampling using the isolation/access catheter.

Figure 1:
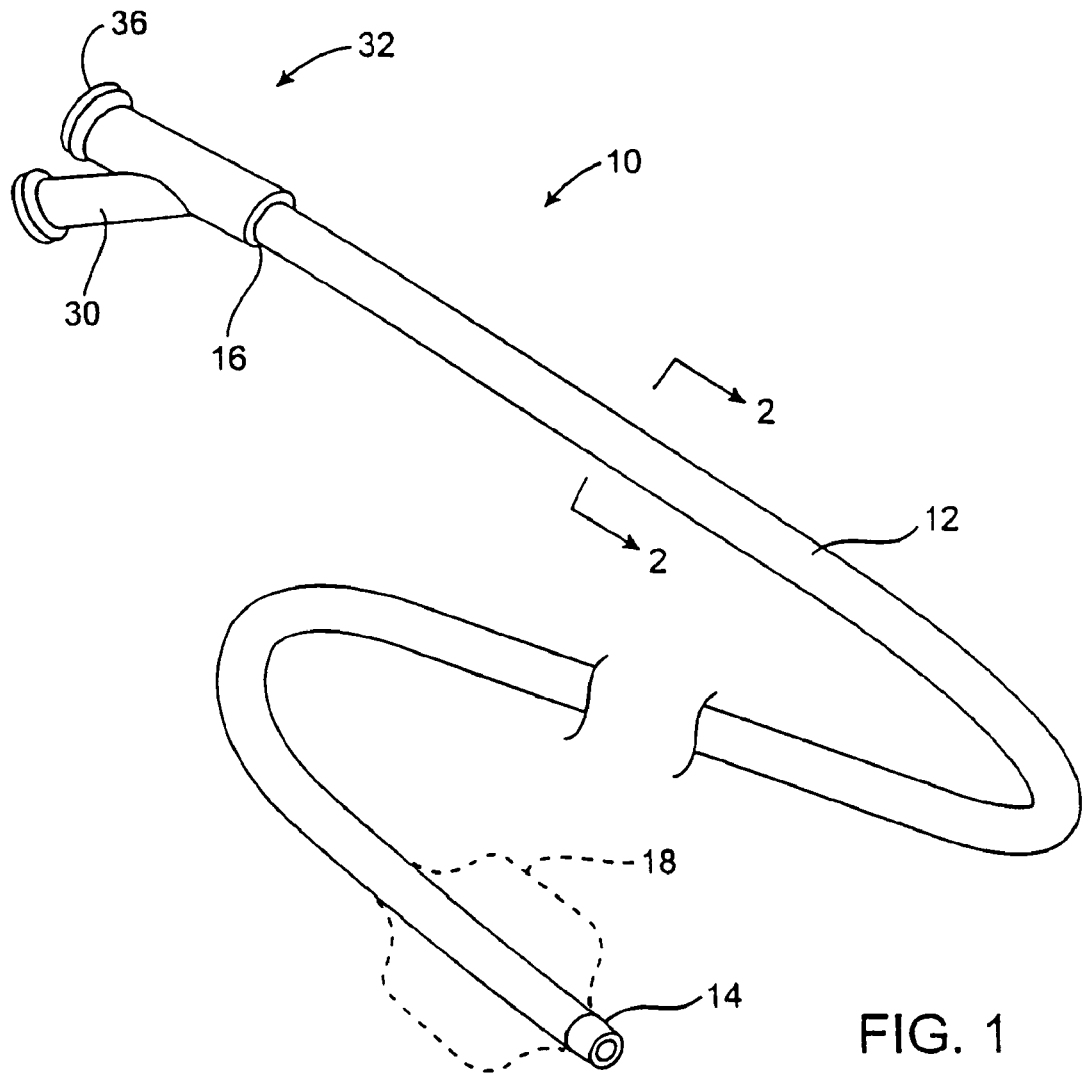
FIG. 1 is a perspective illustration of an isolation/access catheter useful in the methods, systems, and kits of the present invention.
Figure 2:
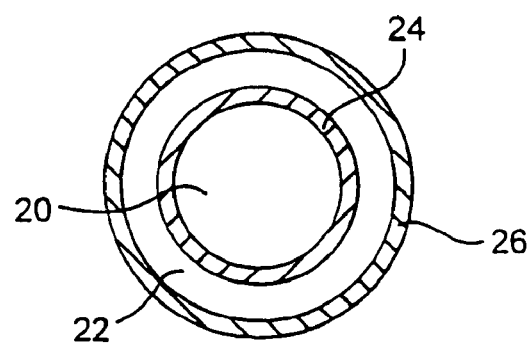
FIG. 2 is a cross-sectional view taken along line 2 to a FIG. 1.

The methods of the present invention will generally rely on accessing the target lung tissue segment using an isolation/access catheter adapted to be introduced endotracheally into the bronchus of the lung. An exemplary isolation/access catheter 10 is illustrated in FIGS. 1 and 2 and comprises a catheter body 12 having a distal end 14, a proximal end 16, an inflatable occlusion balloon 18 near its distal end, and at least one lumen therethrough. Usually, the catheter will have at least two lumens, and catheter 10 includes both a central lumen 20 and an annular lumen 22 defined by inner body member 24 and outer body member 26 which is coaxially disposed about the inner body member. The annular lumen 22 opens to port 30 on a proximal hub 32 and provides for inflation of balloon 18. The central lumen 20 opens to port 36 on hub 32 and provides for multiple functions, including optional introduction over a guidewire, aspiration, introduction of secondary catheters, such as sealing catheters described below, and the like.

Figure 4A:
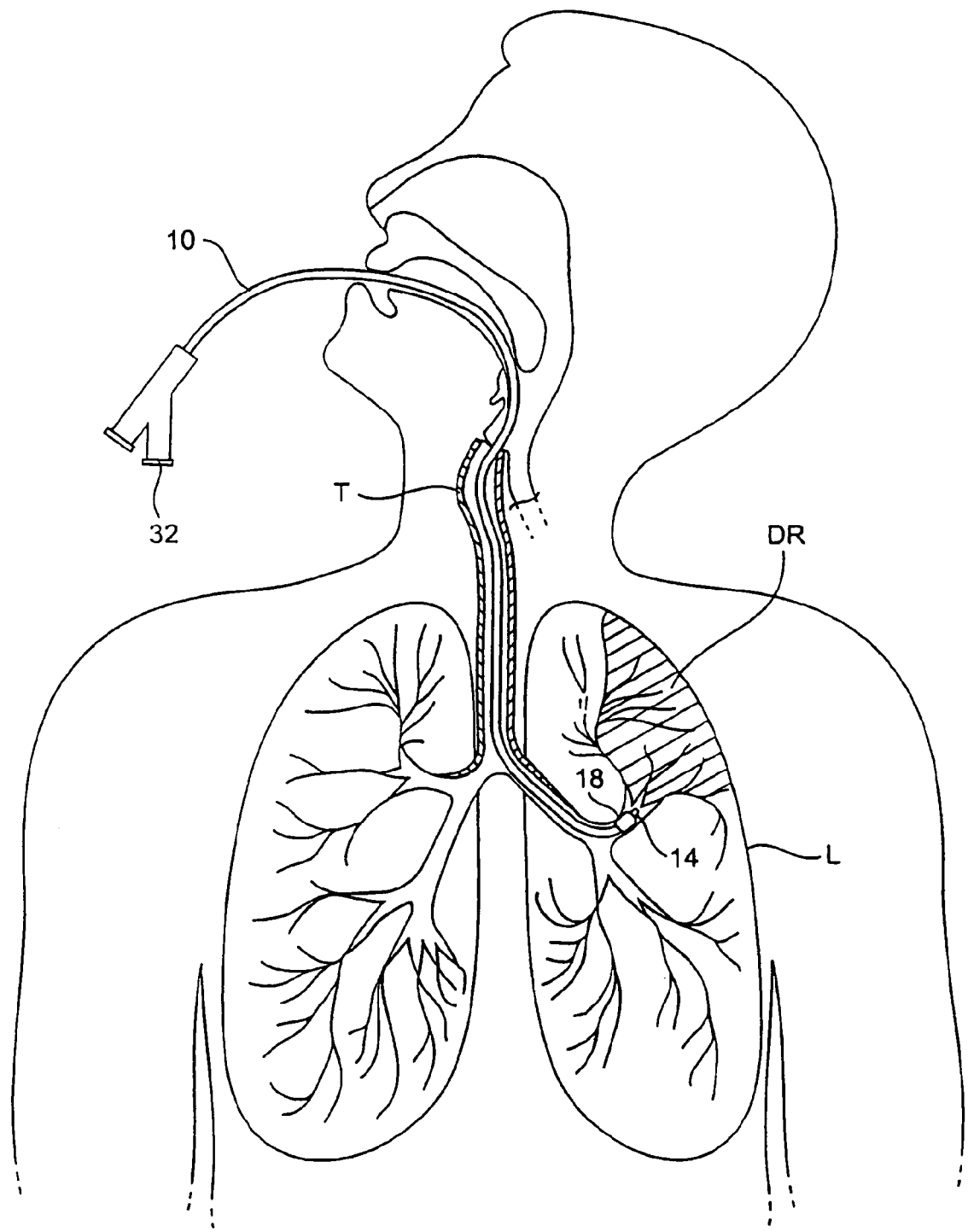
FIGS. 4A-4C illustrate use of the isolation/access catheter of FIG. 1 for isolating and collapsing a target lung tissue segment according the to the methods of the present invention.
Figure 4B:
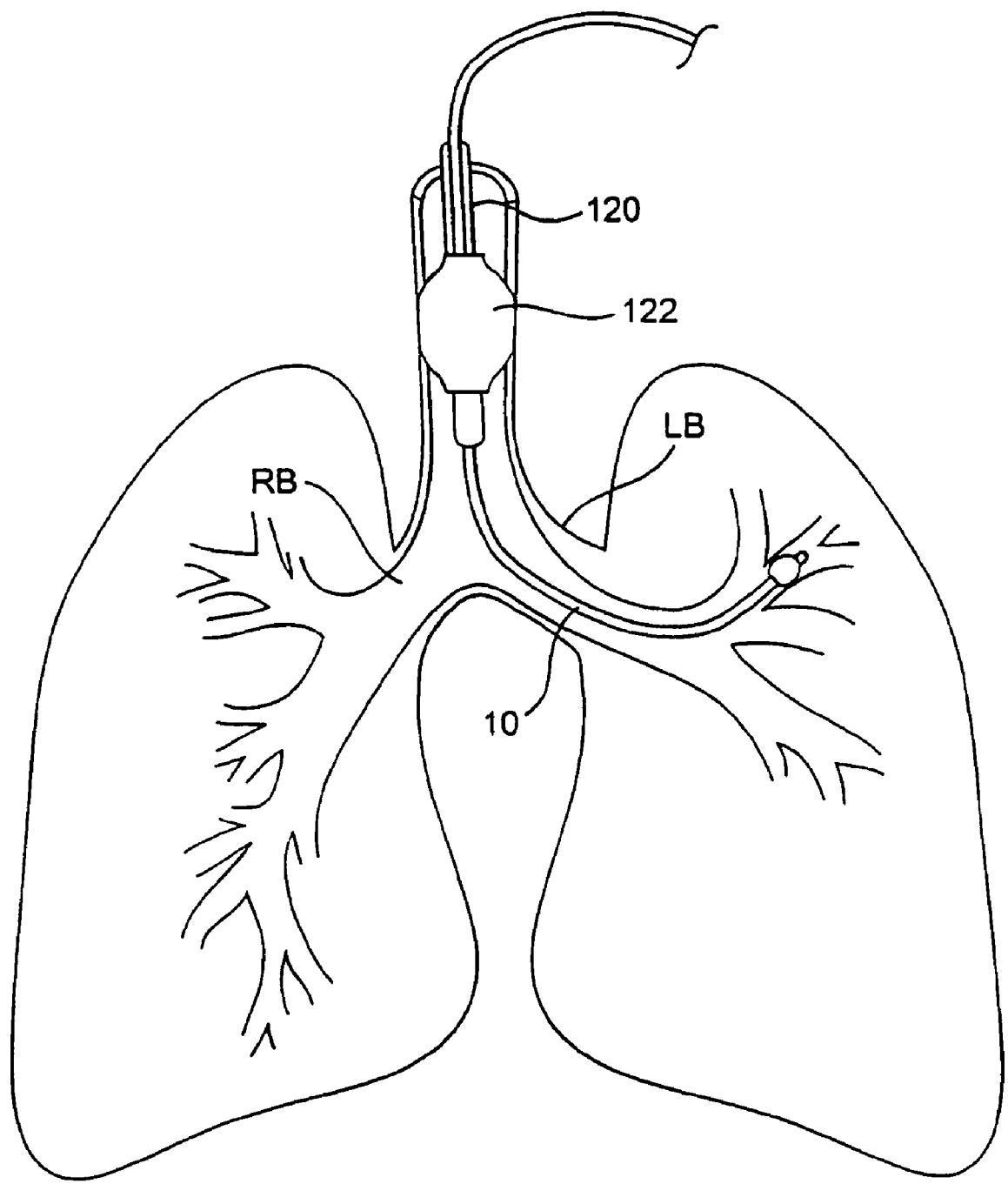

The dimensions and materials of isolation/access catheter 10 are selected to permit endotracheal introduction and intraluminal advancement through the lung bronchus, optionally over a guidewire and/or through a primary tracheal tube structure (as illustrated in FIG. 4B below). Suitable materials include low and high density polyethylenes, polyamides, nylons, PTFE, PEEK, and the like, particularly for the inner tubular member 24. The outer member, including the occlusion balloon, can be made from elastomeric materials, such as polyurethane, low density polyethylene, polyvinylchloride, silicone rubber, latex, and the like. Optionally, portions of the outer tubular member 26 proximal to the inflatable balloon can be made thicker and/or reinforced so that they do not dilate upon pressurization of the balloon. Exemplary dimensions for the isolation/access catheter 10 are set forth in the table below.

ISOLATION/ACCESS CATHETER DIMENSIONS

| | Exemplary | | Preferred | |
| --- | --- | --- | --- | --- |
| | Inner Tubular Member | Outer Tubular Member | Inner Tubular Member | Outer Tubular Member |
| Outer Diameter (mm) | 0.4-4 | 0.6-4.5 | 1-1.5 | 2-4 |
| Wall Thickness (mm) | 0.05-0.25 | 0.5-0.25 | 0.1-0.2 | 0.15-0.25 |
| Length (cm) | 50-150 | same | 50-80 | same |
| Balloon Length (mm) | 5-50 | | 10-20 | |
| Balloon Diameter (mm) (inflated) | 2-15 | | 6-12 | |

Figure 3A:
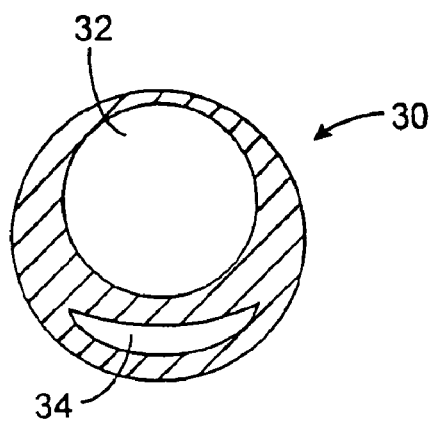
FIGS. 3A-3F illustrate alternative cross-sectional views of the isolation/access catheter of FIG. 1.
Figure 3B:
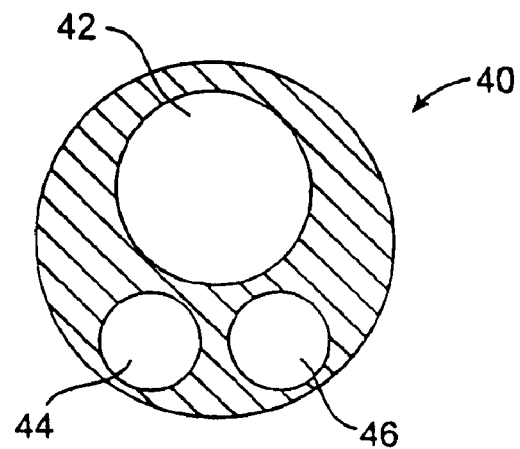
Figure 3C:
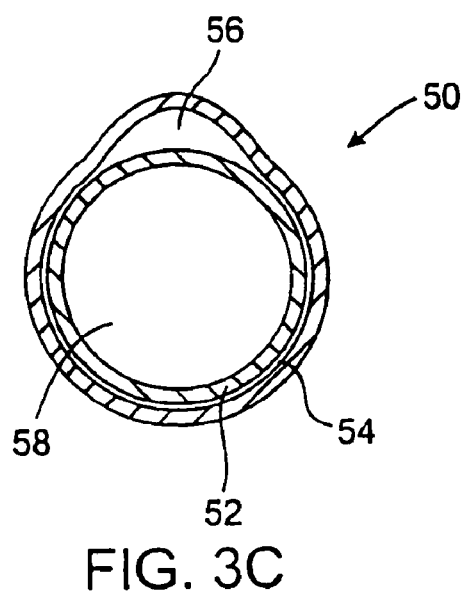
Figure 3D:
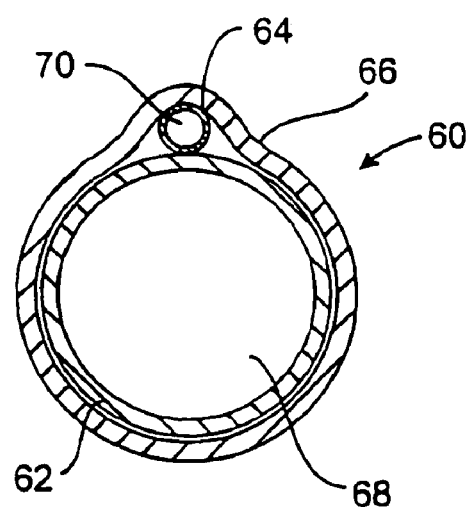

The isolation/access catheter 10 may be modified in a number of ways, some of which are illustrated in FIGS. 3A-3F. For example, instead of a inner and outer coaxial tube construction, the catheter can be a single extrusion having a catheter body 30 with a circular main lumen 32 and a crescent-shaped inflation lumen 34, as illustrated in FIG. 3A. Alternatively, catheter body 40 may be formed as a single extrusion having three lumens, i.e., a primary lumen 42 for receiving a guidewire, applying aspiration, and/or delivering secondary catheters. A second lumen 44 can be provided for inflating the occlusion balloon, and a third lumen 46 can be provided as an alternative guidewire or aspiration lumen. Catheter body 50 comprising a main tubular body 52 having an outer layer 54 fused thereover to define a lumen 56 suitable for balloon inflation as shown in FIG. 3C. A primary lumen 58 is formed within the main tubular member 52. As a slight alternative, catheter body 60 can be formed from a primary tubular member 62, and a secondary tubular member 64, where the tubular members are held together by an outer member 66, such as a layer which is applied by heat shrinking. The primary tubular member 62 provides the main lumen 68 while secondary tube 64 provides a secondary lumen 70. The secondary lumen 70 will typically be used for balloon inflation, while the primary lumen 68 can be used for all other functions of the isolation/access catheter.

Figure 3E:
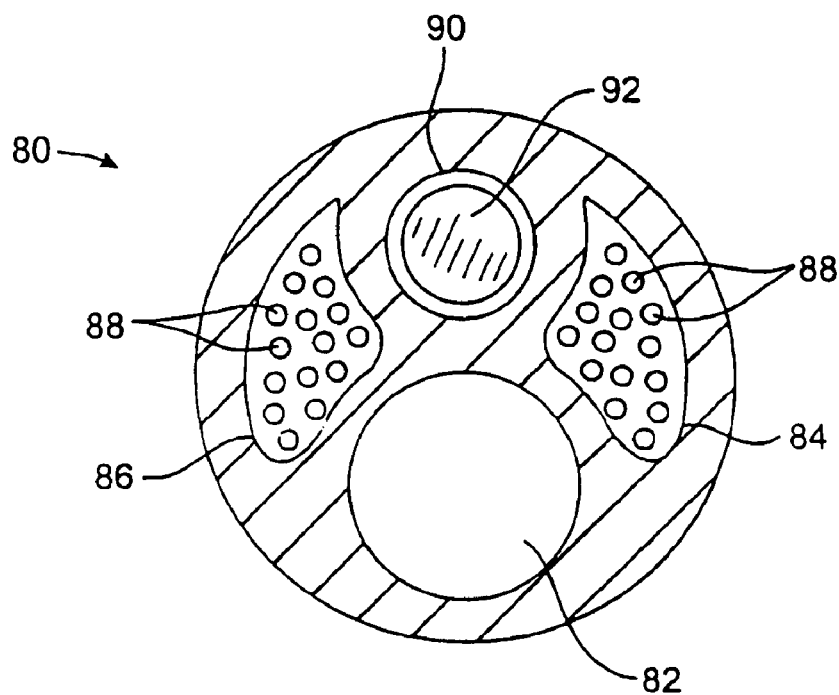
Figure 3F:
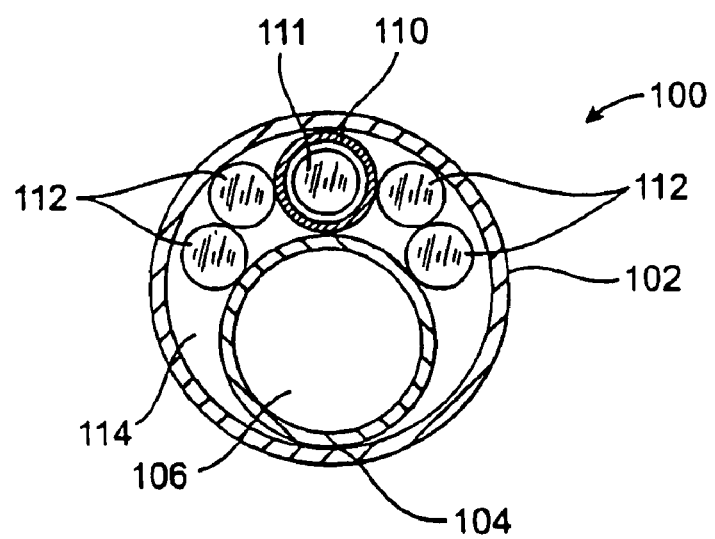

Optionally, the isolation/access catheter in the present invention can be provided with optical imaging capability. As shown in FIG. 3E, catheter body 80 can be formed to include four lumens, typically by conventional extrusion processes. Lumen 82 is suitable for passage over a guidewire. Lumens 84 and 86 both contain light fibers 88 for illumination. Lumen 90 carries an optical wave guide or image fiber 92. Lumen 82 can be used for irrigation and aspiration, typically after the guidewire is withdrawn. Balloon inflation can be effected through the space remaining and lumens 84 and 86 surrounding the light fibers 88. A second catheter body 100 is formed as a coaxial arrangement of a number separate tubes. Outer tube 102 contains a separate guidewire tube 104 defining lumen 106 which permits introduction over a guidewire as well as perfusion and aspiration after the guidewire is removed. Second inner tubular member 110 will carry an optical image fiber 112 and a plurality of light fibers 112 are passed within the remaining space 114 within the outer tubular member. In both catheter constructions 80 and 100, forward imaging can be effected by illuminating through the light fibers and detecting an image through a lens at the distal end of the catheter. The image can be displayed on conventional cathode-ray or other types of imaging screens. In particular, as described below, forward imaging permits a user to selectively place the guidewire for advancing the catheters through a desired route through the branching bronchus.

Referring now to FIG. 4A, a catheter 10 can be advanced to a diseased region DR within a lung L through a patient's trachea T. Advancement through the trachea T is relatively simple and will optionally employ a guidewire to select the advancement route through the branching bronchus. As described above, steering can be effected under real time imaging using the imaging isolation/access catheters illustrated in FIGS. 3E and 3F. Optionally, the isolation/access catheter 10 may be introduced through a visualizing tracheal tube, such as that described in U.S. Pat. No. 5,285,778, licensed to the assignee of the present application. The visualizing endotracheal tube 120 includes an occlusion cuff 122 which may be inflated within the trachea just above the branch of the left bronchus and right bronchus LB and RB, respectively. The visualizing endotracheal tube 120 includes a forward-viewing optical system, typically including both illumination fibers and an image fiber to permit direct viewing of the main branch between the left bronchus LB and right bronchus RB. Thus, initial placement of isolation/access catheter can be made under visualization of the visualizing endotracheal tube 120 and optionally the isolation/access catheter 10 itself. Referring again in particular to FIG. 4A, the isolation/access catheter 10 is advanced until its distal end 14 reaches a region in the bronchus which leads directly into the diseased region DR. Once in place, the balloon 18 can be inflated and the lung tissue segment which includes the diseased region isolated from the remainder of the lung. By isolated, it is meant that air or other gases will not pass between the isolated region and the remaining portions of the lung to any significant extent.

Figure 4C:
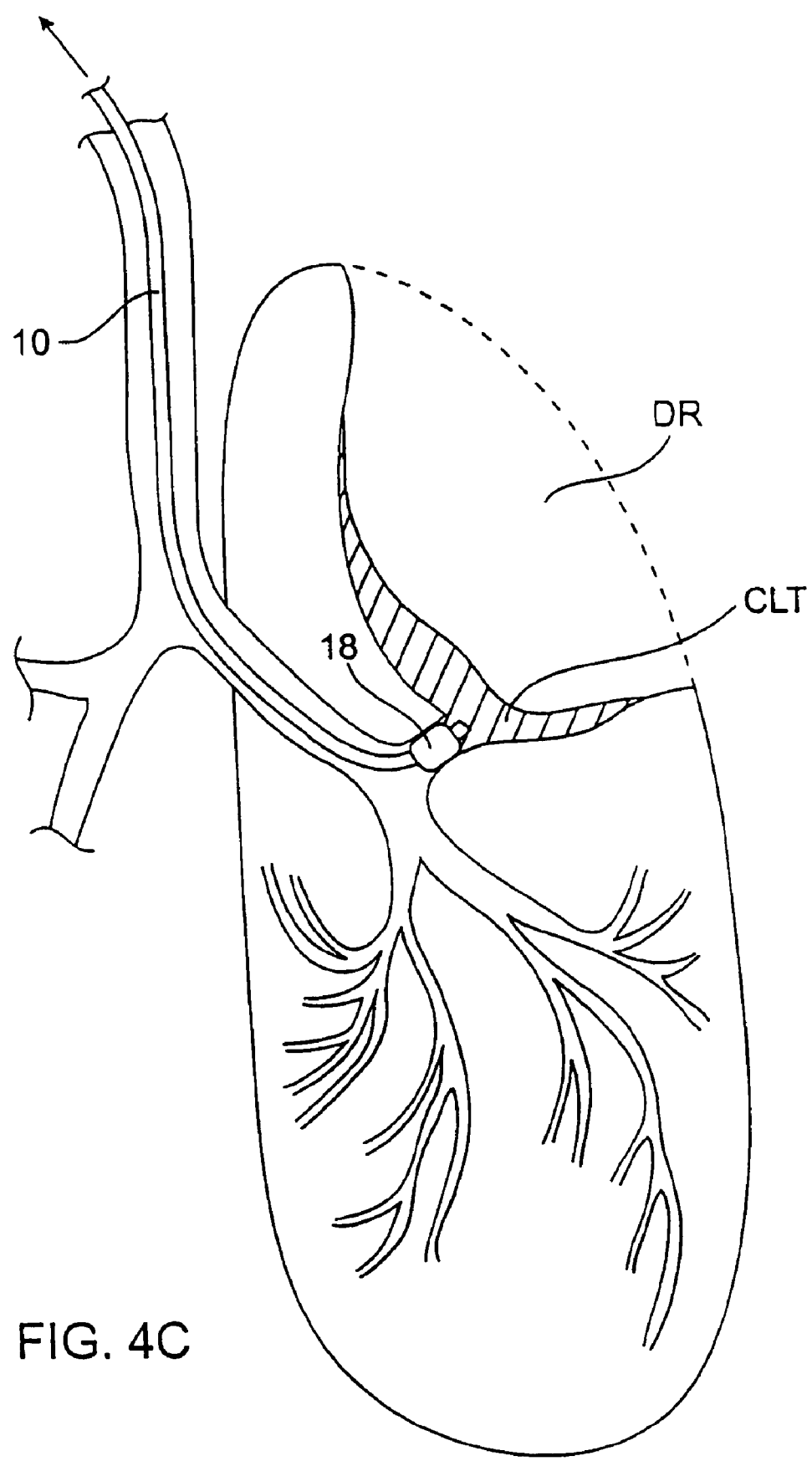

As shown in FIG. 4C, it is the object of the present invention to apply a vacuum to a lumen within the isolation/access catheter 10 to aspirate the internal regions within the isolated lung tissue segment in order to collapse the tissue. This results in a collapsed lung tissue region CLT, as shown as a shaded region in FIG. 4C.

According to the present invention, a variety of steps and protocols may be performed prior to aspirating the isolated lung tissue region in order to enhance gas removal from the region. The region may be over inflated, subjected to vibrations, subjected to a dilating or mucolytic agent, or otherwise treated in order to remove gas flow obstructions within the region. Each of these methods has been well described above and will generally rely on performance of at least one aspect of the procedure using a lumen of the isolation/access catheter 10. For example, over inflation can be effected simply by introducing an inflation gas through the isolation/access catheter to a desired pressure. Pressure may be measured using a transducer at the distal tip of the catheter 10, but will usually be measured statically at a location proximal of the catheter. Alternatively or additionally, an oxygen-rich gas can be introduced through the isolation/access catheter in order to induce absorption atelectasis. For vibratory stimulation incompressible fluid may be introduced through the isolation/access catheter. Stimulation may be imparted using an external probe and/or a vibratory catheter which is introduced through an access lumen of the isolation/access catheter.

Figure 4D:
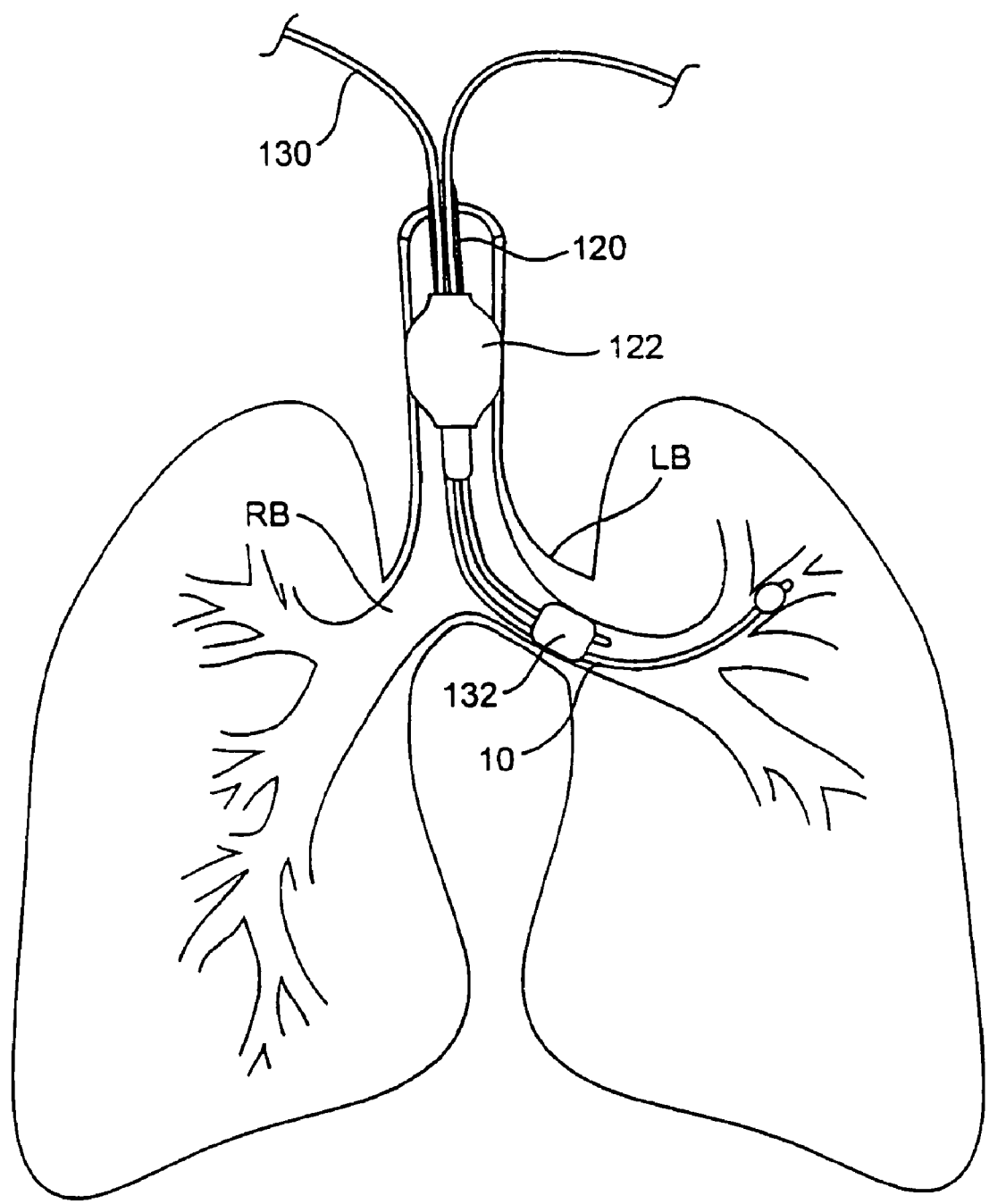
FIG. 4D illustrates one protocol for over inflating a target lung tissue segment prior to aspiration according to the present invention.

As shown in FIG. 4D, in some instances it will be desirable to reduce or selectively control the inflation of the lung tissue adjacent to the target lung tissue segment in order to enhance aspiration of the target segment. For example, an entire one-half lung can be selectively controlled by an isolation or shunting catheter having a balloon 132 near its distal end. The balloon is inflated to occlude a portion of the selected bronchus, typically about 60% of the area. Thus, pressure within the lung can be reduced and the lung partly collapsed other than in the isolated region. In this way, inflation of the target lung tissue segment can be enhanced which can assist in breaking up occlusions within the lung which would otherwise interfere with subsequent aspiration of the segment.

Figure 5:
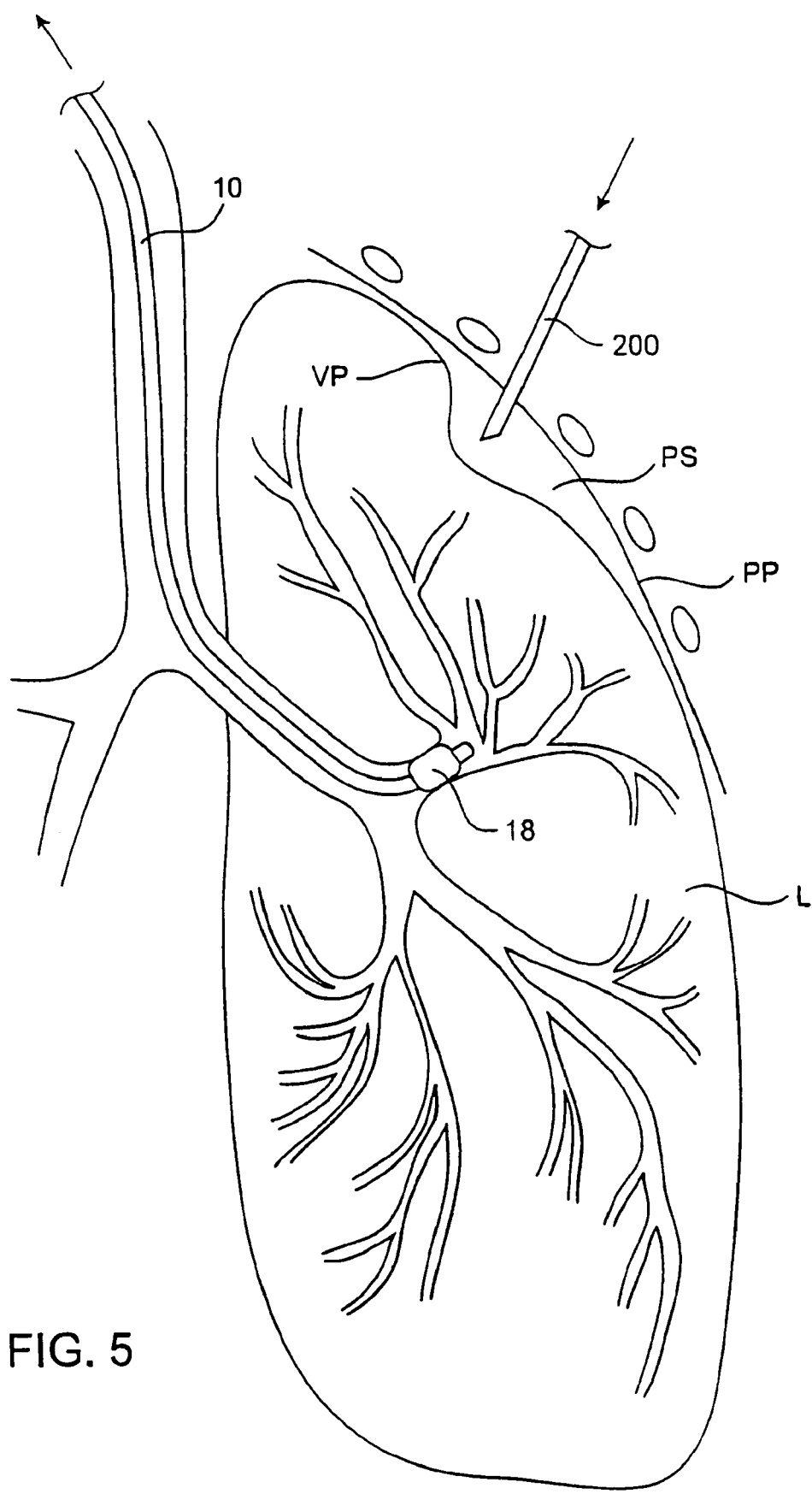
FIG. 5 illustrates an optional aspect of the present invention where an insufflation gas is introduced to aid in the collapse of the target segment from the pleural space.
Figure 6:
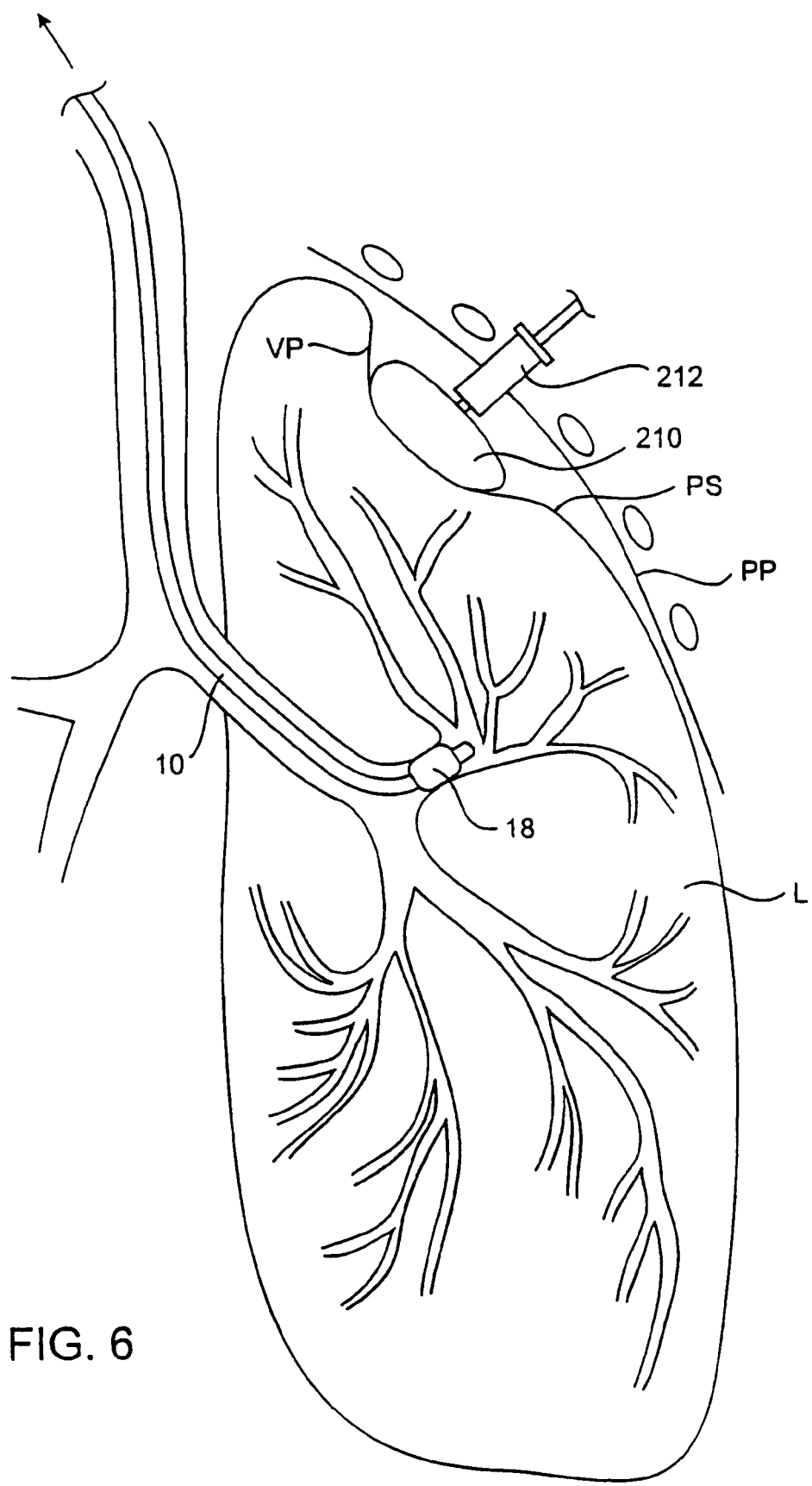
FIG. 6 illustrates an alternative optional aspect of the present invention where an inflatable balloon is used to externally collapse a portion of a target lung tissue segment.

In addition to such in situ techniques for enhancing lung aspiration and collapse, the present invention can rely on application of an external force to assist in collapse. As illustrated in FIG. 5, a needle or other cannula 200 can be percutaneously introduced into a peritoneal space PS between the parietal pleural PP and visceral pleural VP. Insufflation gas, such as carbon dioxide, can be introduced through the needle 200, either using a syringe or other pressure source. The gas will typically be introduced to a pressure in the range from 30 cm $H_2O$ to 200 cm $H_2O$ in spontaneously breathing patients and 70 cm $H_2O$ to 250 cm $H_2O$ in positive pressure ventilated patients.

Figure 7A:
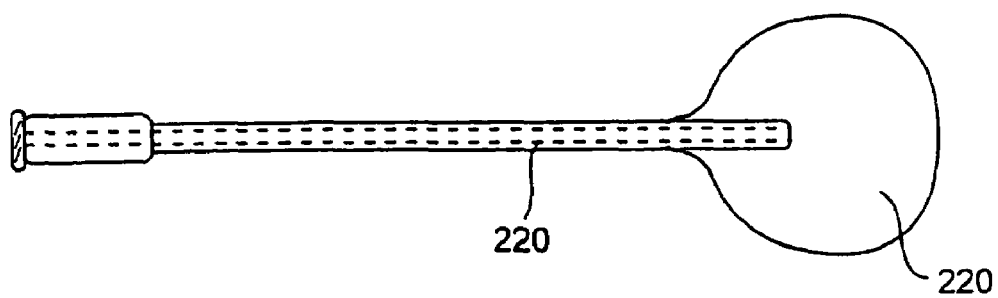
FIGS. 7A-7D illustrate alternative balloon designs for use in external collapse of the target lung tissue segment.
Figure 7B:
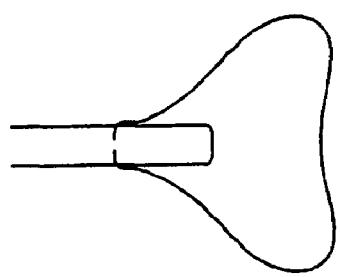
Figure 7C:
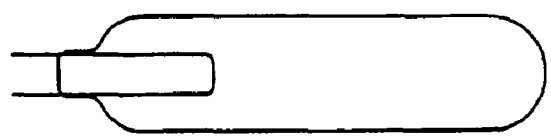
Figure 7D:
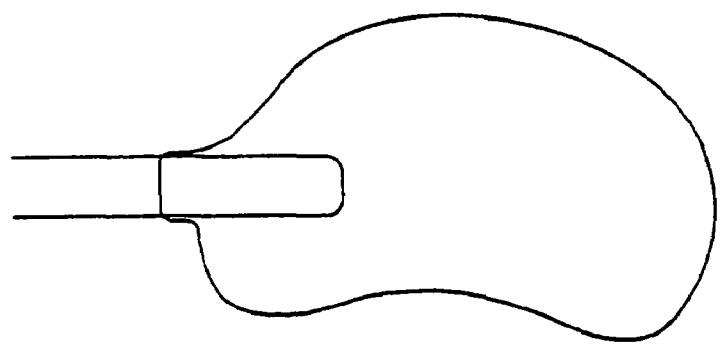

Use of an unconstrained insufflation gas, however, is disadvantageous since it is not directed at a particular target location. In order to more specifically direct an external pressure against the lung, a balloon 210 can be introduced to the pleural space, typically through a thoracic trocar 212. The balloon can be placed based on fluoroscopic observation. Depending on the particular area which is to be collapsed, a variety of specific balloon configurations can be employed, as illustrated in FIGS. 7A-7D. A generally spherical balloon 220 is shown attached to shaft 220 in FIG. 7A. Other configurations include a winged profile (FIG. 7B), a cylindrical or spatula profile (FIG. 7C), and a convex profile (FIG. 7D). Each of these will be attached to a shaft which permits inflation after introduction into the pleural space.

Figure 8:
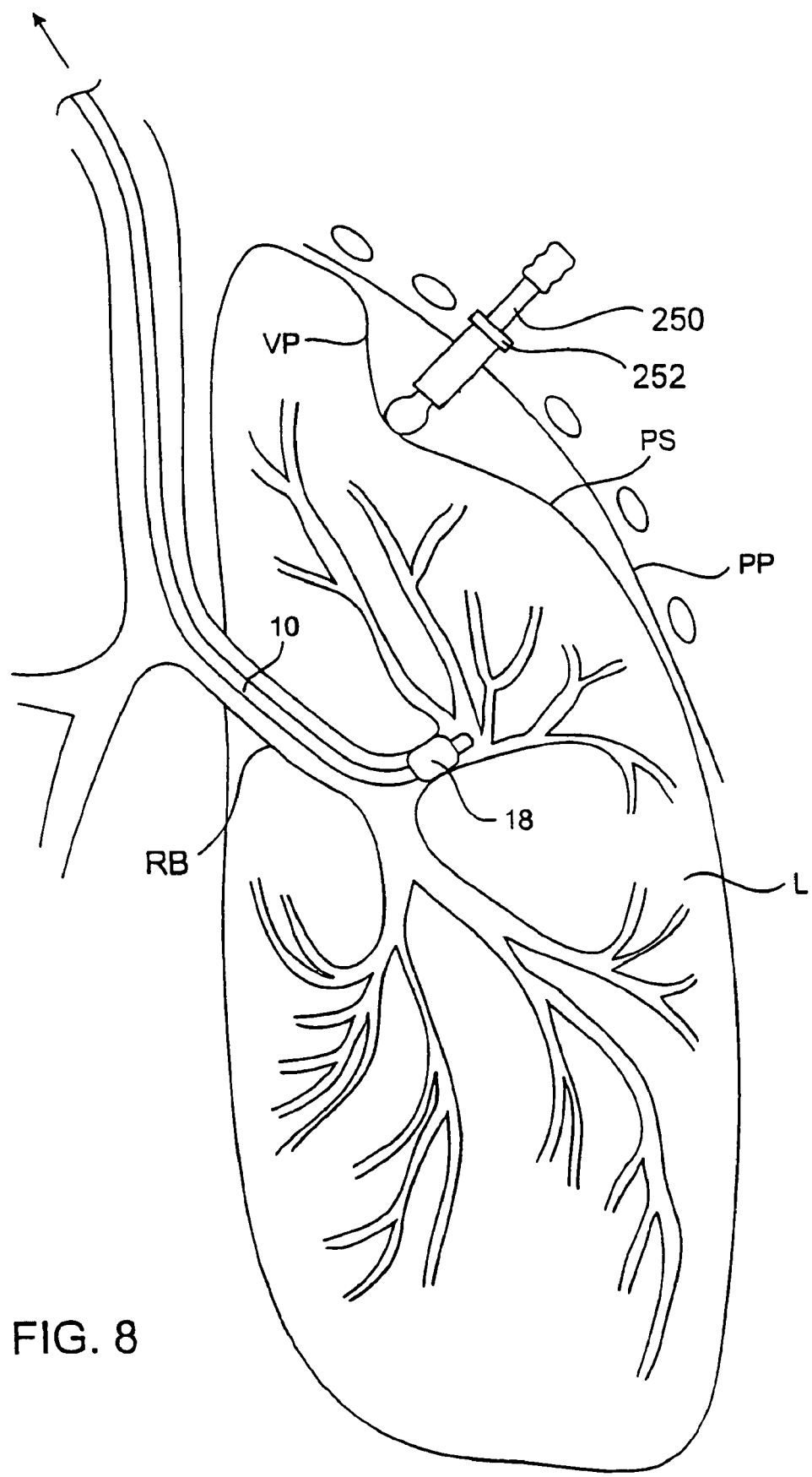
FIG. 8 illustrates yet another alternative optional aspect of the methods of the present invention where a probe is used to engage and collapse a portion of a target lung tissue segment.
Figure 9A:
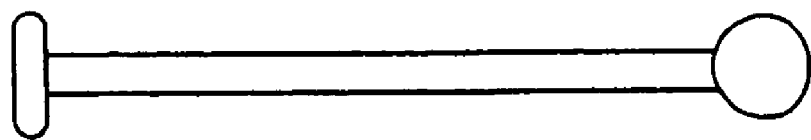
FIGS. 9A-9C illustrate alternative probe designs.
Figure 9B:
Figure 9C:
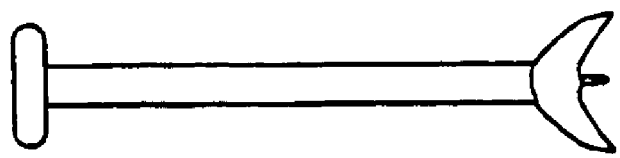

As a further alternative to needle insufflation and balloon expansion, a target lung tissue segment can be externally collapsed using a simple probe 250, usually introduced through a thoracic trocar 252, as shown in FIG. 8. A variety of probes for mechanically engaging and compressing the outer lung surface are illustrated in FIGS. 9A-9C. Optionally, a needle can be used to puncture at a desired point in the target tissue lung segment in order to release and/or aspirate air, usually as a supplement to a primary catheter-based aspiration. The puncture can then be sealed with fibrin glue or other suitable sealant.

Figure 10A:
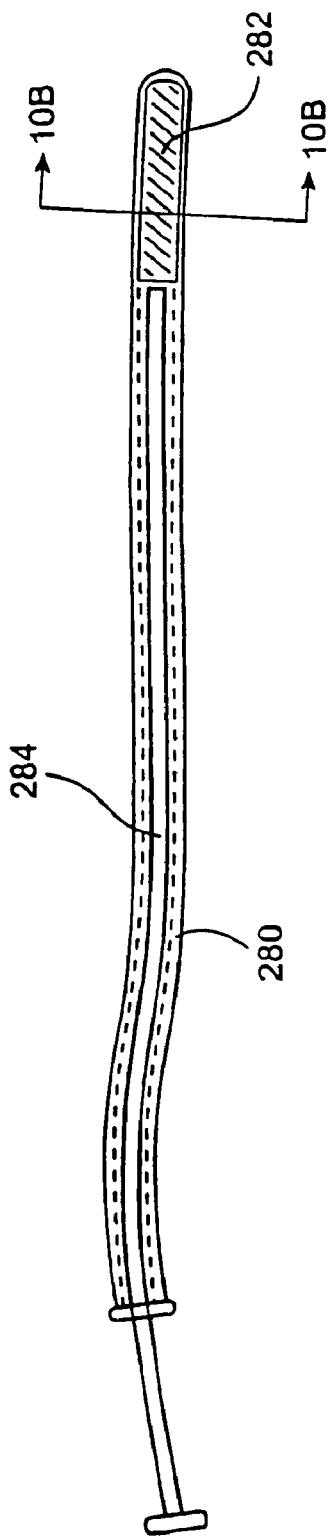
FIGS. 10A-10C illustrate a sealing catheter carrying a swellable closure element which may be used in the methods, systems, and kits of the present invention.
Figure 10C:
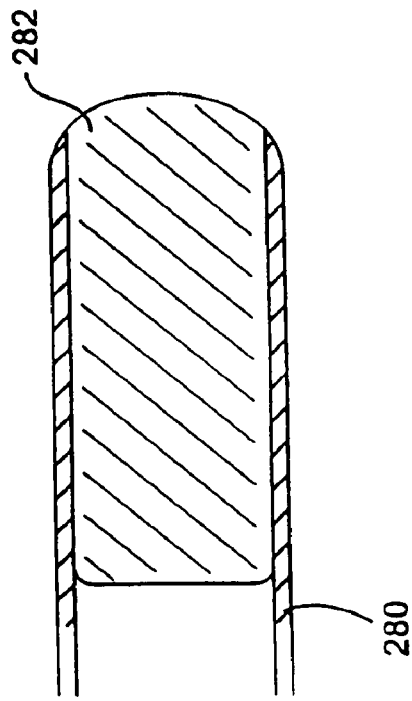
Figure 10B:
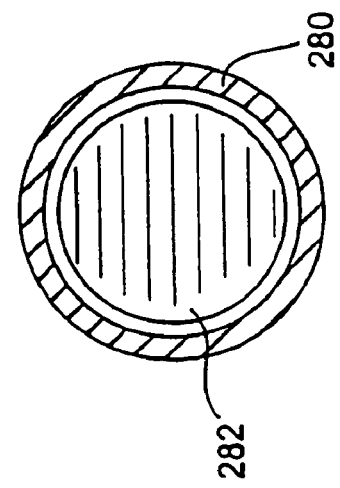
Figure 11:
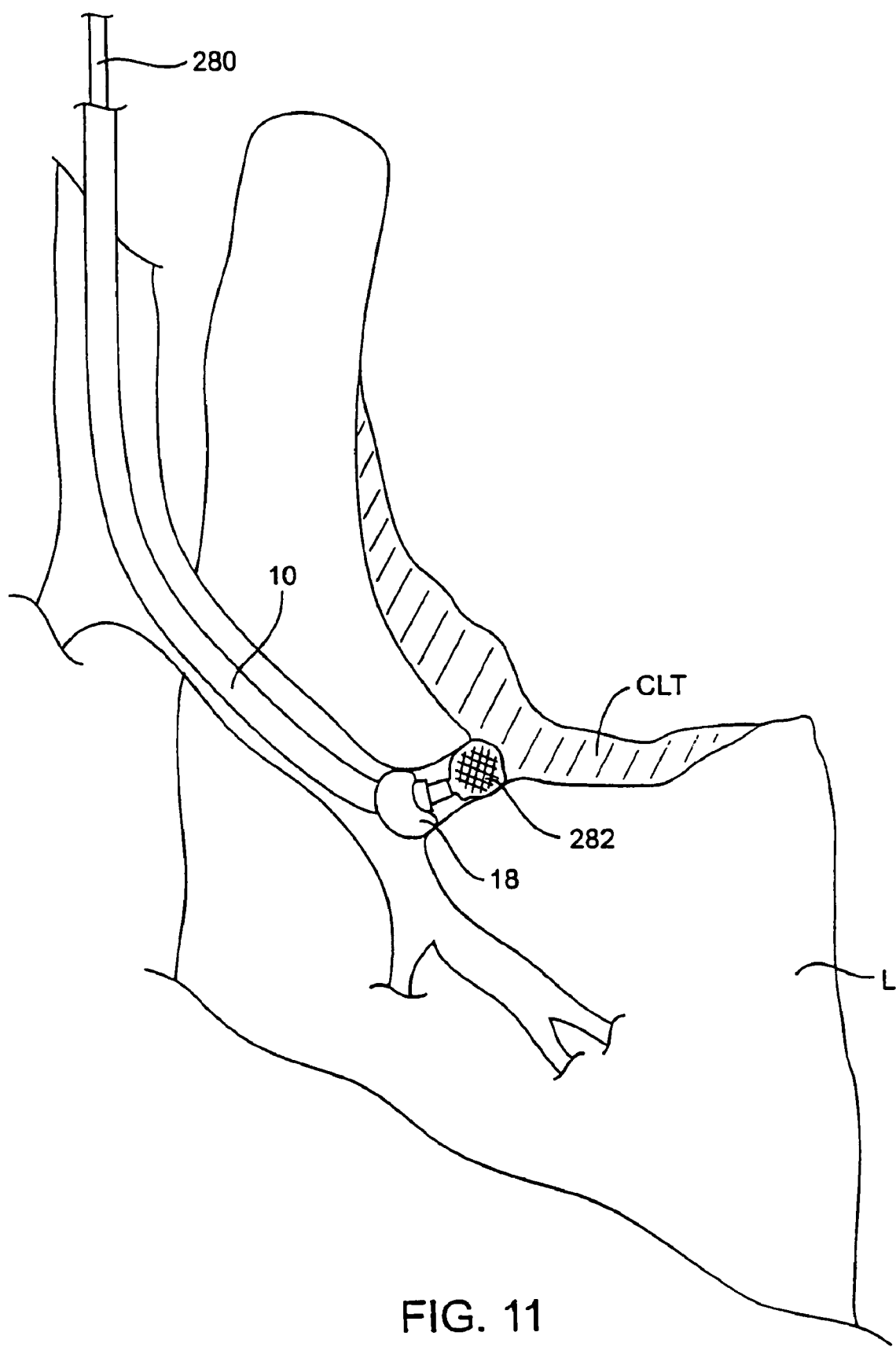
FIG. 11 illustrates use of the sealing catheter of FIGS. 10A-10C for selectively occluding an air passage leading to a target lung tissue segment according to the methods of the present invention.

The methods of the present invention will optionally comprise sealing or occluding the air passage leading to the collapsed tissue region CLT. Such sealing can be performed in a variety of ways, including suturing, gluing, energy-mediated tissue adhesion, and the like. In a preferred aspect of the present invention, a sealing catheter 280 can be used to deliver a plug 282, typically at partially hydrated collagen hydrogel, as illustrated in FIGS. 10A-10C. Usually, the catheter will have dimensions which permit it to be introduced through the main access lumen of isolation/access catheter 10. The plug 282 will be contained in the distal tip of a lumen in the catheter, and a push rod 284 extends the length of the catheter to permit the treating physician to deploy the plug 282 after the tip of the catheter is properly located, as illustrated in FIG. 11, usually while the balloon on the isolation/access catheter remains inflated and the target lung tissue remains sealed and in an aspirated, collapsed configuration. Once deployed within the moist environment of the lung bronchus, the plug 282 will absorb water and will swell substantially, typically from 100% to 1000% in order to fully occupy and plug the air passage into the collapsed lung tissue region CLT.

Figure 12A:
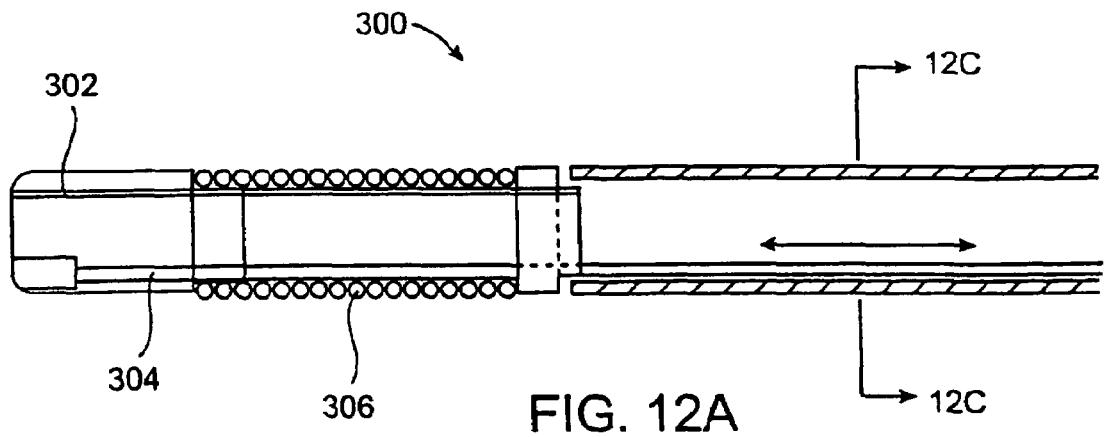
FIGS. 12A-12C illustrate a steerable imaging guidewire which may be used to facilitate positioning of the isolation/access catheter used in the methods of the present invention.
Figure 12B:
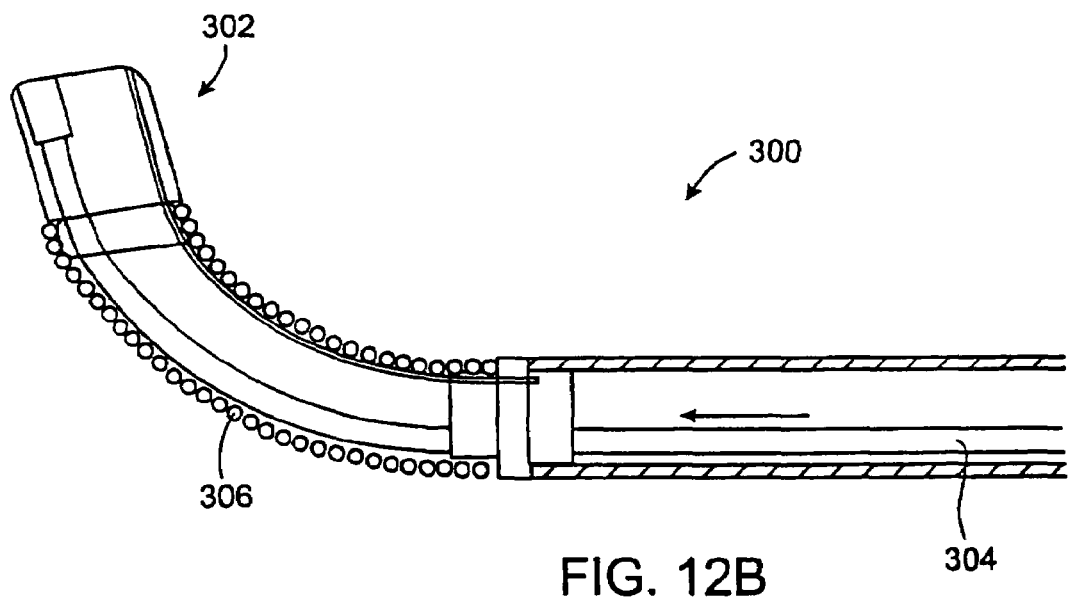
Figure 12C:
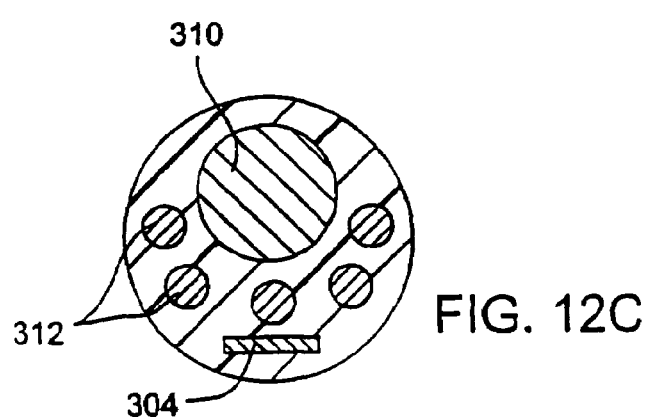

Positioning of the isolation/access catheter 10 within the lung can be performed using on-board optical imaging capability, as discussed above. Usually, positioning of a guidewire through the branching bronchus will be manipulated while viewing through the imaging components of the isolation/access catheter. In this way, the isolation/access catheter can be "inched" along by alternately advancing the guidewire and the isolation/access catheter. As an alternative to providing the isolation/access catheter with imaging, positioning could be done solely by fluoroscopy. As a further alternative, a steerable, imaging guidewire 300 (FIGS. 12A-12C) could be used. The guidewire 300 includes a deflectable tip 302 which can be deflected in a single plane using push/pull ribbon 304. Usually, the tip will comprise a spring 306 to facilitate deflection. In addition to steerability, the guidewire 300 will include an optical imaging wave guide 310 and illuminating optical fibers 312, as best seen in cross-sectional view of FIG. 12C. Thus, the guidewire 300 can be steered through the branching bronchus to reach the target tissue segment using its own in situ imaging capability. Once the guidewire 300 is in place, an isolation/access catheter can be introduced to the target lung tissue segment as well. Since the guidewire has imaging capability, the isolation/access catheter need not incorporate such imaging. This can be an advantage since it permits the access lumen to be made larger since the catheter need not carry any optical wave guides.

Figure 13:
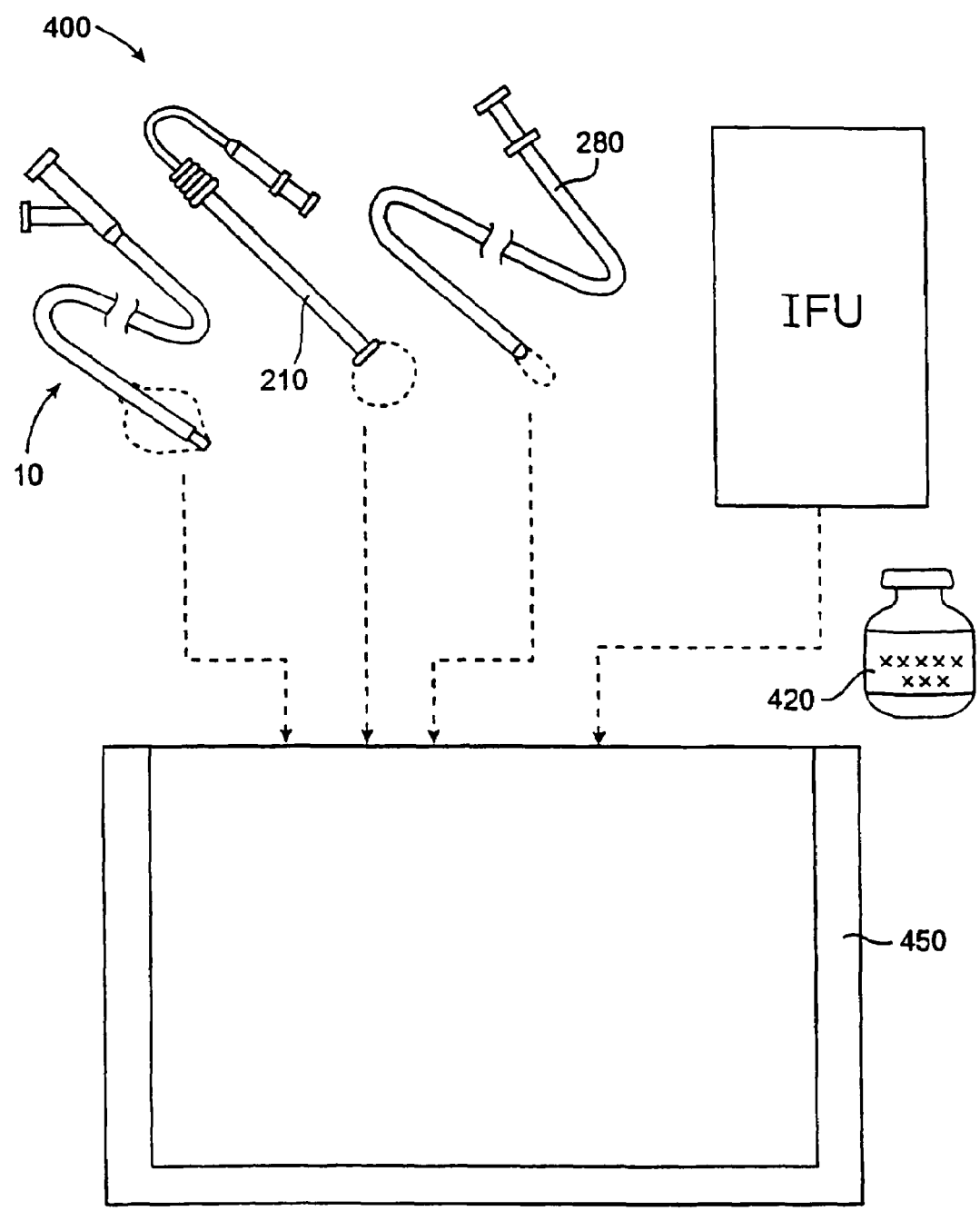
FIG. 13 illustrates a kit constructed in accordance with the principles of the present invention.

Referring now to FIG. 13, kits 400 according to the present invention comprise at least an isolation/access catheter 10 and instructions for use IFU. Optionally, the kits may further include any of the other system components described above, such as a balloon probe 210, a sealing catheter 280, a reagent container 420 (optionally including any of the dilating or mucolytic agents described above), or other components. The instructions for use IFU will set forth any of the methods as described above, and all kit components will usually be packaged together in a pouch 450 or other conventional medical device packaging. Usually, those kit components, such as isolation/access catheter 10, which will be used in performing the procedure on the patient will be sterilized and maintained sterilely within the kit. Optionally, separate pouches, bags, trays, or other packaging may be provided within a larger package, where the smaller packs may be opened separately and separately maintain the components in a sterile fashion.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of reducing lung size of a lung, the method including the steps of:

inserting a conduit down a trachea, into a mainstem bronchus, into a bronchial branch, and into a bronchial sub-branch communicating with a lung portion of the lung to be reduced in size;

pulling a vacuum in the lung portion through the conduit to collapse the lung portion; and deploying an obstructing member in the bronchial sub-branch to preclude air from being inhaled into the lung portion through the bronchial sub-branch.

2. The method of claim 1, wherein the deploying step includes feeding the obstructing member down the conduit and into the bronchial sub-branch.

3. A method for lung volume reduction, said method comprising:

isolating a lung tissue segment;

aspirating the isolated segment to cause the segment to collapse; and sealing an air passage which opens to the lung segment to inhibit reinflation of the segment.

4. The method of claim 3, wherein sealing comprises deploying a plug in the air passage.

5. The method of claim 4, wherein deploying comprises advancing the plug through a catheter to the air passage.

* * * * *